(12) United States Patent
Igaki et al.

(10) Patent No.: US 7,652,228 B2
(45) Date of Patent: Jan. 26, 2010

(54) STEAM-GENERATING WARMING ARTICLE

(75) Inventors: Michihito Igaki, Tokyo (JP); Koichi Okisaka, Tokyo (JP); Ichiro Sakamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 407 days.

(21) Appl. No.: 10/582,232

(22) PCT Filed: Dec. 16, 2004

(86) PCT No.: PCT/JP2004/018797

§ 371 (c)(1),
(2), (4) Date: Dec. 6, 2006

(87) PCT Pub. No.: WO2005/058213

PCT Pub. Date: Jun. 30, 2005

(65) Prior Publication Data

US 2007/0110790 A1      May 17, 2007

(30) Foreign Application Priority Data

Dec. 16, 2003   (JP) ............................. 2003-418734

(51) Int. Cl.
*A21B 1/00* (2006.01)
*A61F 13/00* (2006.01)

(52) U.S. Cl. ............ 219/401; 126/263.05; 126/263.06; 126/263.04; 126/263.01; 126/204; 607/109; 607/114; 424/443; 252/70; 165/46

(58) Field of Classification Search ............ 126/263.05, 126/263.06, 263.04, 263.01, 204; 219/401; 607/109, 114; 424/443; 252/70; 165/46
See application file for complete search history.

(56) References Cited

U.S. PATENT DOCUMENTS

| 6,409,746 B1 | 6/2002 | Igaki et al. |
| 6,823,860 B2 | 11/2004 | Igaki et al. |
| 2005/0000827 A1* | 1/2005 | Matsui et al. ............... 205/689 |

FOREIGN PATENT DOCUMENTS

| EP | 0 786 240 | 7/1997 |
| EP | 0 856 302 | 8/1998 |
| JP | 1 201253 | 8/1989 |

(Continued)

OTHER PUBLICATIONS

U.S. Appl. No. 12/295,314, filed Sep. 30, 2008, Igaki, et al.

*Primary Examiner*—Shawntina Fuqua
(74) *Attorney, Agent, or Firm*—Oblon, Spivak, McClelland, Maier & Neustadt, L.L.P.

(57) ABSTRACT

A steam-generating warming article 1 which has a steam generating element 2 making use of chemical energy and is adapted to supply steam while in contact with a human body. The article 1, while in contact with the body, maintains the skin surface temperature at 38° to 49° C. for 3 to 15 hours and cumulatively generates 0.5 to 12 mg/3 hr·cm$^2$ of steam. The steam-generating warning article 1 is used to improve the human body's physiology. The steam generating element 2 is preferably a heat generating sheet prepared by incorporating an aqueous electrolyte solution into a molded sheet containing an oxidizable metal, a reaction accelerator, and a fibrous material.

14 Claims, 8 Drawing Sheets

FOREIGN PATENT DOCUMENTS

| | | |
|---|---|---|
| JP | 7 59809 | 3/1995 |
| JP | 10-146355 | 6/1998 |
| JP | 2002-58699 | 2/2002 |
| JP | 2002-65714 | 3/2002 |
| JP | 2002-78727 | 3/2002 |
| JP | 2003-24361 | 1/2003 |
| JP | 2003-102761 | 4/2003 |
| JP | 2003-102761 A | 4/2003 |
| JP | 2004-359508 | 12/2004 |

* cited by examiner

STEAM-GENERATING WARMING ARTICLE

TECHNICAL FIELD

The present invention relates to a steam-generating warming article. The present invention also relates to a steam-generating warming sheet as a kind of steam-generating warming article.

BACKGROUND ART

There have been changes in attitude toward middle age with the changes of lifestyles, and middle-aged and senior persons who care about maintaining a high quality of everyday life, so called "active seniors", are increasing. The health-consciousness of society overall shows an inclination toward self-medication. With this trend, awareness of daily health care is increasing among the active seniors.

Typical health problems common to persons of middle-age and older are lower back pain, shoulder pain, sensitivity to cold temperatures, blurred vision, and the like. From now on, to alleviate, cure or prevent these symptoms through daily life at home will be a popular choice among the middle-aged and senior adults. Taking for instance, heat therapy with a disposable heat pack body warmer (a heating element containing oxidizable metal) applied to the affected part, e.g., the lower back is known to help provide pain relief. It is expected that such heat therapy will become increasingly popular on the individual level.

In this connection, JP-A-2002-65714 and JP-A-2002-78727 propose an eye mask-type vision improving device and an eye mask-type meibomian gland function improving device which both supply steam to and around the eyes. These treating devices supply steam at temperatures safe to the body to and around the eyes thereby to relax and improve the ciliary muscle, improve the vision, or improve the meibomian gland function. Since the devices are designed to be applied to and around the eyes, the time of supplying steam is so short as not to adversely affect these parts of the body, i.e., several tens of minutes at the most. These devices aim at improvement of vision or the meibomian gland function. The cited publications do not mention whether the devices are capable of relieving lower back pain, abdominal pain, and the like.

Apart from the treating devices, JP-A-2003-102761 discloses a thin heat-generating sheet as a heat generating element that can be used for heat therapy. The sheet is extremely thin and yet exhibits excellent heat generating characteristics as a heat generating element. The sheet is characterized by a uniform thickness and high productivity. There still is an increase in demand for a heat generating sheet producing still higher therapeutic effects in step with the aging of the population.

DISCLOSURE OF THE INVENTION

The present invention provides a steam generating warming article which has a steam generating element making use of chemical energy and is adapted to supply steam while in contact with the surface of the body. While in contact with the surface of the body, the steam-generating warming article maintains the skin surface temperature at 38° to 49° C. over a period of 3 to 15 hours and has a steam generating ability such that a cumulative amount of released steam ranges from 0.5 to 12 mg/3 hr·cm$^2$.

The present invention also provides a method of using the steam-generating warming article, wherein the steam-generating warming article is applied to the surface of the body to supply steam and maintain the skin surface temperature at 38° to 49° C. over a period of 3 to 15 hours.

The present invention also provides a steam-generating warming sheet having a heat generating sheet and a holder for holding the heat generating sheet. The heat generating sheet is a molded sheet containing an oxidizable metal, a reaction accelerator, and a fibrous material and having incorporated therein an aqueous solution of an electrolyte and is capable of heat generation on contact with air. The holder has air permeability in at least a part thereof so that warming steam may be released from the heat generating sheet through the holder to the outside. The molded sheet contains 60% to 90% by weight of an oxidizable metal, 5% to 25% by weight of a reaction accelerator, and 5% to 35% by weight of a fibrous material. The heat generating sheet has incorporated therein 40 to 80 parts by weight of an aqueous solution containing 1 to 15% by weight of an electrolyte per 100 parts by weight of the molded sheet. The air permeable part of the holder has a water vapor transmission rate of 300 to 2000 g/m$^2$·24 hr (JIS Z0208, 40° C., 90% RH).

DETAILED DESCRIPTION OF THE INVENTION

Figure 1:
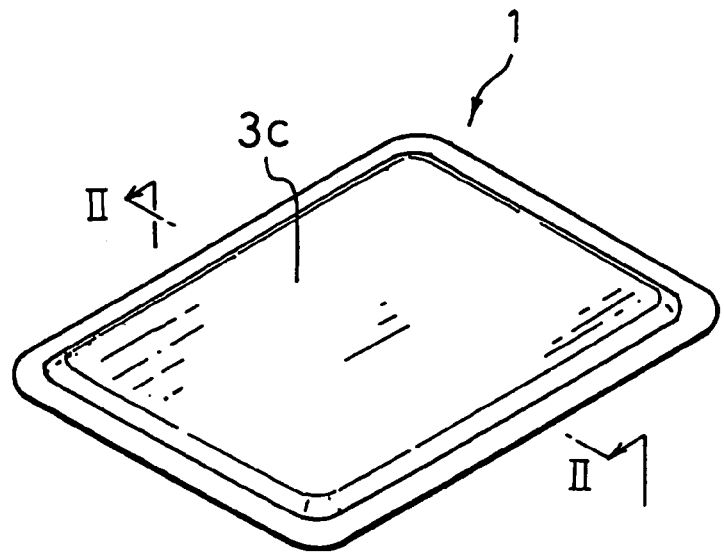
FIG. 1 is a perspective view of a steam-generating warming sheet as an embodiment of a steam-generating warming article according to the present invention.

The present invention provides a steam generating warming article with which to improve various physiological functions of the human body. The steam-generating warming article of the present invention is applied to the body surface. The body part to which it is applied is not limited and includes any part of the body such as the lower back, the abdomen, the neck, shoulders, and various joints. The steam-generating warming article of the present invention is particularly suitable to be applied to the lower back or shoulders to promote blood circulation. The steam generating warming article is used in contact with the body surface. The term "in contact with" as used herein is intended to include being in direct contact with the skin and being in indirect contact with the skin with an intermediate permeable to water vapor.

While worn by a wearer, the steam generating warming article of the present invention elevates not only the surface temperature of the part where it is applied but the deep body temperature. This brings about an increase in the overall blood flow and a rise in not only the temperature of the part of the body but the peripheral temperature of, for example, fingers. An effect in maintaining the peripheral temperature is also experienced. Accordingly, the steam-generating warming article of the invention offers benefits such as promotion of blood flow, elimination of muscle tiredness, reduction of muscle stiffness, relaxation of sore muscles, reduction of sensitiveness to cold temperatures, and alleviation of nerve pain. Where a steam-generating warming sheet described infra, a kind of steam-generating warming article, is applied to a part of the body, it fits well without giving a wearer discomfort because of its softness.

The deep body temperature is thought to correspond to the temperature of a tissue 10 mm deep from the skin. When a rise in deep body temperature is up to 0.2° C., an appreciable rise in the finger tip surface temperature is not confirmed. When a rise in deep body temperature is 0.3° C. or more, a rise or maintenance of the finger tip surface temperature is confirmed. Likewise, warming of finger tips and the whole body cannot be felt with a deep body temperature rise of 0.2° C. or less but is noticeably felt when a deep body temperature rise is 0.3° C. or more.

The steam generating warming article has a steam generating element that generates steam by making use of chemical energy and is characterized in that steam generated from the element is applied to the body surface. The steam-generating warming article is notably characterized by its long duration of steam generation. In the following description the heat accompanied by steam is referred to as moist heat. In contrast to moist heat, heat that is not accompanied by steam, such as heat from a commercially available disposable body warmer, is referred to as dry heat.

Moist heat is preferably heat by steam capable of increasing the deep body temperature by at least 0.3° C. In the present invention, steam having such capability will be called "warming steam". Moist heat is heat accompanied by steam generation. The term "skin surface temperature" as used herein denotes the temperature of the skin surface measured with a contact thermometer, for example, a thermocouple.

The chemical energy that can be made use of in the present invention includes heat of oxidation generated by the oxidation reaction of an oxidizable metal, heat of neutralization generated by a neutralization reaction between an acid and an alkali, and a heat of hydration of an inorganic salt (e.g., calcium chloride, magnesium chloride, calcium oxide, magnesium oxide or zeolite). It is preferred to use, among them, heat of oxidation by oxidation reaction of an oxidizable metal in view of ease of handling because of process dryness, a relatively high heat value, and the possibility of providing an easy-to-carry, compact product.

The composition of the steam generating element is decided as appropriate according to the type of the chemical energy to be utilized. For example, in using heat of oxidation generated by the oxidation reaction of an oxidizable metal, the steam generating element is made of a steam generative composition containing a powdered metal (e.g., iron, aluminum, zinc or copper), a salt as a catalyst (e.g., an alkali metal chloride such as sodium chloride or potassium chloride or an alkaline earth metal chloride such as calcium chloride or magnesium chloride), and water. The steam generative composition can contain a moisture retaining agent (e.g., vermiculite, calcium silicate, silica gel, silicic porous substances, alumina, pulp, wood meal or water-absorbent polymers), a reaction accelerator (e.g., activated carbon, carbon black or graphite) if desired.

In using heat of neutralization between an acid and an alkali or heat of hydration of an inorganic salt, the steam generating element can be composed of a heating part where the heat of neutralization or hydration is generated and an evaporation part where water vapor is released by the heat generated from the heating part. In the heating part the reactants are separated by a partition. The partition is broken whenever steam generation is demanded to allow the reaction to proceed. The evaporation part is made of, for example, a fiber aggregate (such as paper, woven fabric or nonwoven fabric) or a porous material impregnated with water or a water-containing polymer gel drawn into sheeting and is configured to release water vapor by the heat generated in the heating part.

While in contact with the surface of the body, the steam-generating warming article of the present invention maintains the skin surface temperature at 38° to 49° C., preferably 38° to 43° C., over a period of 3 to 15 hours, preferably 3 to 10 hours, and has a steam generating ability such that a cumulative amount of released steam ranges from 0.5 to 12 mg/3 hr·cm$^2$, preferably 4 to 9 mg/3 hr·cm$^2$. Applying the steam generating warming article having the recited steam generating ability to the surface of the body brings about remarkable improvements on various physiological functions of the human body as will be demonstrated in Examples given later.

The terminology "cumulative amount of released steam" denotes the total amount of water vapor cumulatively released in three hours from the initiation of a chemical reaction in the steam generating element. The cumulative amount of released steam is measured as follows. A steam-generating warming article is placed in a closed chamber having a volume of 54000 cm$^3$ (50 cm (W)×36 cm (L)×30 cm (H)) and conditioned at 20° C. and 40% RH in such a mariner that the article is allowed to release steam in the chamber. A chemical reaction is induced in the steam generating warming article, and the humidity of the air in the chamber is measured with a hygrometer to calculate the amount of water vapor generated after the commencement of the reaction. The cumulative amount of the water vapor generated up to 3 hours from the commencement of the reaction is obtained.

In order for the steam-generating warming article to have the recited steam generating ability, the highest temperature reached by the steam generating warming article through chemical energy-induced heat generation is preferably 38° C. or higher. To prevent a cold burn, the highest reachable temperature of the steam-generating warming article is preferably 60° C. or lower. The highest temperature reached is measured in accordance with JIS S4100.

The steam generating warming article is used as applied to the human body, such as the lower back, the abdomen or a shoulder, with its portion from which steam is released facing to the body. As a result of the inventors' study, it has been revealed that warming the lower back, the abdomen or shoulder with moist heat results in greater promotion of systemic blood flow and a greater rise in the peripheral temperature than with commercially available disposable body warmers generating little steam, namely dry heat. It has also been found that the body temperature continues to rise for several tens of minutes even after moist heat application is stopped. The inventors have investigated into the reason why and found, as a result, that moist heat enjoys high heat conductivity and is capable of elevating not only the skin surface temperature of the part where it is applied but also the deep body temperature. It is considered that a rise in temperature deep in the body stimulates the heat center, whereby autonomic equilibrium shifts towards predominance of the parasympathetic tone. It seems to follow that the blood vessels dilate to increase the blood flow and to raise the peripheral temperature. It is also believed that an increased blood flow removes a pain producing substance, thereby resulting in the alleviation or elimination of pain. Thus, the steam-generating warming article is effective in not only elevating the temperature of the body part where it is applied and improving the blood flow but also relieving or eliminating the pain of the part, removing tiredness from muscles, decrease of muscle stiffness or soreness, and relieving nerve pain. It is additionally effective in improving the blood flow all over the body, elevating or maintaining the peripheral temperatures such as the finger tip temperatures, and reducing sensitiveness to cold temperatures.

For example, application of the steam-generating warming article to the lower back relieves or eliminates lower back pain as demonstrated in Examples given later, and application to the abdomen relieves or eliminates abdominal pain caused by constipation, diarrhea, etc. Application to the lower back and/or the abdomen also results in improvement of visceral functions such as gastrointestinal functions and recovery from physical fatigue. While heat therapy with dry heat has long been practiced, it is a fact first discovered by the inventors that various physiological functions of the human body are remarkably improved by using moist heat, particularly by supplying moist heat with the steam-generating warming article having the above recited steam generating ability.

How to control the steam generating ability of the steam-generating warming article is decided appropriately according to the kind of chemical energy utilized. For example, the reaction rate is controlled by properly adjusting the amounts of reactants to be reacted in the steam generating element, the particle size of the reactants (if particulate), the rate of feeding the reactants, and so forth, thereby controlling the steam generating ability. It is also possible to control the steam generating ability by adjusting the amount of steam to be transferred to the body surface by interposing a moisture permeable sheet between the steam generating element and the body surface.

Preferred embodiments of the steam-generating warming article according to the present invention will be described with reference to the accompanying drawings.

Figure 2:
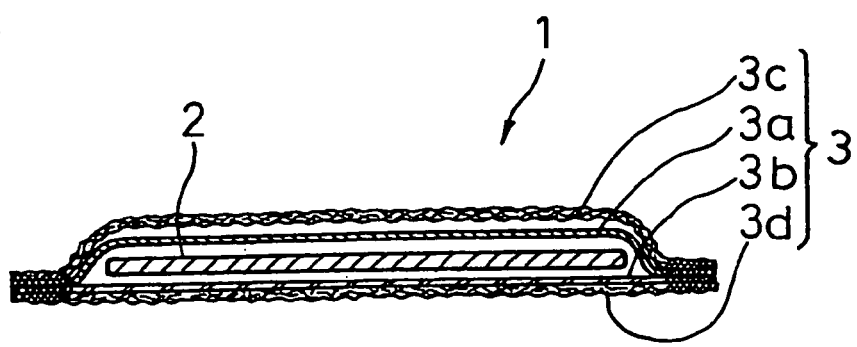
FIG. 2 is a cross-section taken along line II-II in FIG. 1.
Figure 3:
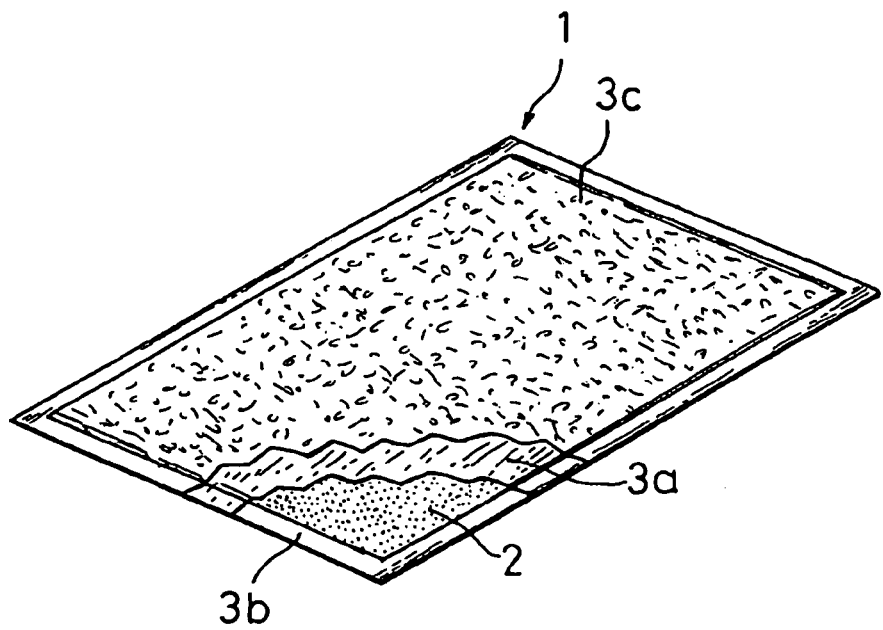
FIG. 3 is a perspective view of another embodiment of a steam-generating warming sheet according to the present invention with a part cut away.
Figure 4:
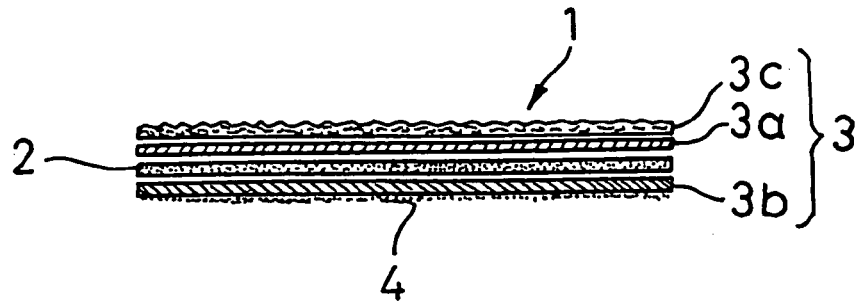
FIG. 4 is a schematic cross-sectional view of the steam-generating warming sheet of FIG. 3.

FIG. 1 illustrates a steam generating warming sheet as an embodiment of the steam-generating warming article of the present invention. FIG. 2 is a cross-sectional view taken along line II-II in FIG. 1. FIG. 3 is a perspective view of another embodiment of a steam-generating warming sheet with a part cut away. FIG. 4 is a schematic cross-sectional view of the steam-generating warming sheet of FIG. 3. The steam-generating warming sheets illustrated in FIGS. 1 and 3 are both flat and rectangular and have a heat generating sheet 2 as a steam generating element and a holder 3 for holding the heat generating sheet 2. As described infra, the heat generating sheet 2 is formed of a fibrous sheet and is slightly smaller in both width and length than the holder 3. The holder 3 is a flat bag and made of two or more sheets whose edges are joined together to make hollow inside. At least a part of the holder 3 is an air permeable part having moisture permeability.

The heat generating sheet 2 is capable of generating heat upon contact with air. For this purpose, the heat generating sheet 2 contains an oxidizable metal, a reaction accelerator, a fibrous material, an electrolyte, and water. As soon as the heat generating sheet 2 comes in contact with air, the oxidizable metal present in the sheet 2 starts being oxidized to generate heat. The water contained in the heat generating sheet 2 is heated by the heat into water vapor (warming steam) of prescribed temperature, which is released outside through the holder 3. The water vapor (warming steam) is released outside through the air permeable part of the holder 3.

As mentioned above, the heat generating sheet 2 contains an oxidizable metal, a reaction accelerator, a fibrous material, and an electrolyte and is wet with water. Specifically, the heat generating sheet 2 is a molded sheet containing an oxidizable metal, a reaction accelerator, and a fibrous material and having incorporated therein an aqueous solution of an electrolyte. Of these materials those largely influential on the above specified steam generating ability of the steam generating warming sheet 1 were found, as a result of the inventors' study, to be the oxidizable metal, the reaction accelerator, and the fibrous material. More specifically, it is meaningful that the molded sheet preferably contains 60% to 90% by weight, more preferably 70% to 85% by weight, of the oxidizable metal, 5% to 25% by weight, more preferably 8% to 15% by weight, of the reaction accelerator, and 5% to 35% by weight, more preferably 10% to 20% by weight, of the fibrous material. With the contents of these materials falling within the recited respective preferred ranges, steam generating ability as desired is expected of the heat generating sheet 2. The molded sheet is suitably prepared by a papermaking process. The molded sheet as formed by papermaking and dried has a water content of 5% by weight or less.

The weight ratio of each of the reaction accelerator and the fibrous material to the oxidizable metal is also influential on the steam generating ability of the steam-generating warming sheet 1. More specifically, the weight ratio of the reaction accelerator to the oxidizable metal in the heat generating sheet 2 is preferably 0.1 to 0.3, more preferably 0.11 to 0.25, and the weight ratio of the fibrous material to the oxidizable metal is preferably 0.1 to 0.3, more preferably 0.12 to 0.29. With the weight ratios falling within the recited preferred ranges, it is easy to raise the skin surface temperature at or above 38° C. as desired, to obtain a desired amount of steam generation, to reach an aimed temperature in a short time after a pillow type package of the steam-generating warming sheet 1 is opened, and to supply moderate moist heat for more than 3 hours.

Other important factors influential on the steam generating ability of the steam-generating warming sheet 1 include the concentration of the aqueous electrolyte solution and the amount of the aqueous electrolyte solution in the heat generating sheet 2. Specifically, the concentration of the aqueous electrolyte solution in the heat generating sheet 2 is preferably 1% to 15% by weight, more preferably 2% to 10% by weight, to obtain a desired temperature. The amount of the aqueous electrolyte solution to be added is preferably 40 to 80 parts by weight, more preferably 50 to 70 parts by weight, per 100 parts by weight of the molded sheet to secure a long duration of a desired temperature and to obtain a desired amount of steam generation.

Other great factors influential on the steam generating ability of the steam-generating warming sheet 1 include the water vapor transmission rate (hereinafter abbreviated as "WVTR") of the holder 3 as measured in accordance with JIS Z0208 at 40° C. and 90% RH. The term "water vapor transmission rate (WVTR)" will hereinafter denote a value measured in the same method. A desired steam generating ability can be obtained by using the heat generating sheet 2 containing the aforementioned components in the aforementioned ratio and using a holder having the following WVTR. Specifically, it is preferred for the air permeable part of the holder 3 to have a WVTR of 300 to 2000 g/m$^2$·24 hr, more preferably 600 to 1000 g/m$^2$·24 hr, to obtain a desired amount of steam release and to achieve a long duration of a desired temperature.

In order to properly control the steam temperature and to secure a duration of steam generation at a desired temperature, it is preferred for the air permeable part of the holder 3 to have an air permeance of 8000 to 15000 s/100 cm$^3$, more preferably 9000 to 12000 s/100 cm$^3$, as measured in accordance with JIS P8117. The term "air permeance" will hereinafter refer to a value measured in the same method. For the same purpose it is preferred for the steam-generating warming sheet to have a steam release area of 0.001 to 0.25 m$^2$, more preferably 0.0025 to 0.04 m$^2$.

While not shown in the figures, the heat generating sheet 2 preferably has a large number of holes and/or cuts, whereby the heat generating sheet 1, while thin, exhibits sufficiently high heat generation characteristics to provide desired warming steam releasing characteristics. Additionally, the holes and/or cuts make the heat generating sheet 2 flexible. As a result, the steam generating warming sheet 1 becomes a better fit when applied to the lower back or any other part of the body, making the wearer feel moistened and warmed more efficiently. Where the heat generating sheet 2 has a large number of holes, the individual holes preferably have an area of 0.01 to 10 mm$^2$, more preferably 0.1 to 8 mm$^2$, to provide sufficient heat generation characteristics. For the same purpose, the number of the holes to be formed per square centimeter is preferably 0.1 to 20, more preferably 1 to 15. The shape of the holes includes a circle, a rectangle, a polygon, an ellipse, an elongated circle, and a combination thereof. Where cuts are made in the heat generating sheet 2, the length of the individual cuts is preferably 1 to 50 mm, more preferably 5 to 30 mm.

To obtain desired heat generation characteristics, two or more heat generating sheets 2 may be used as stacked. In this case, the heat generating sheets 2 are preferably united by embossing to prevent them from sliding on each other while in use. Sliding can also be prevented by making the above-mentioned holes or cuts.

In the embodiments shown in FIGS. 1 through 4, the holder 3 of the steam-generating warming sheet 1 is formed by joining a moisture permeable film 3a and a moisture hardly-permeable film 3b along their perimeters to make a flat bag. That is, one side of the holder 3 has the moisture permeable film 3a, and the other side has the moisture hardly-permeable film 3b. The moisture permeable film 3a allows passage of the steam from the heat generating sheet 2, whereas the moisture hardly-permeable film 3b lets through little steam. Steam is released from only one side of the holder 3, i.e., the side of the moisture permeable film 3a. The WVTR and the air permeance of the moisture permeable film 3a are in the respective ranges specified previously. The steam-generating warming sheet 1 thus exhibits the above specified steam generating ability.

The moisture permeable film 3a to be used is a film that allows passage of warming steam but hardly allows water to pass through. Such a film includes polyolefin films with fine pores. Since steam is released outside through the moisture permeable film 3a, the steam-generating warming sheets 1 of these embodiments are worn with their side of the moisture permeable film 3a facing the wearer's body. Then, a nonwoven fabric 3c having a soft feel, such as air-through nonwoven, is provided on the outer side of the moisture permeable film 3a to give an improved wearing comfort as shown in FIGS. 1 to 4. Accordingly, while the steam generating warming sheet 1 is worn, it is the nonwoven fabric 3c that faces the body.

The moisture hardly-permeable film 3b to be used is a film that allows passage of little water vapor or little water, including nonporous polyolefin films and nonporous polyester films. To improve the feel of the steam-generating warming sheet 1, a nonwoven fabric 3d, such as air-through nonwoven, is provided on the outer side of the moisture hardly-permeable film 3b as shown in FIG. 2. Otherwise, a pressure sensitive adhesive layer 4 is provided on the outer side of the moisture hardly-permeable film 3b as shown in FIG. 4 so that the steam-generating warming sheet 1 may be attached to an attachment belt hereinafter described. The adhesive layer 4 is protected with a sheet of release paper (not shown) until use.

The materials constituting the heat generating sheet 2 will be described in detail. The oxidizable metal includes powder or fiber of iron, aluminum, zinc, manganese, magnesium, and calcium. Iron powder is preferred among them in view of ease in handling, safety, and production cost. Taking fixability onto the fibrous material and reaction controllability into consideration, the oxidizable metal powder preferably has a particle size of 0.1 to 300 μm. For the same reasons, it is also preferred to use powder containing at least 50% by weight of particles having a particle size of 0.1 to 150 μm.

The reaction accelerator is preferably selected from materials serving as a moisture-retaining agent and also having a function as an agent for retaining and supplying oxygen to the oxidizable metal. Examples of such materials include activated carbon (including coconut shell charcoal, charcoal powder, bituminous coal, peat, and lignite), carbon black, acetylene black, graphite, zeolite, pearlite, vermiculite, and silica. Preferred of them is activated carbon in view of its water retaining capability, oxygen feeding capability, and catalyzing ability. The reaction accelerator preferably has a particle size ranging from 0.1 to 500 μm for effective contact with the oxidizable metal. For the same reason, it is also preferred for the reaction accelerator to contain at least 50% by weight of particles having a particle size of 0.1 to 200 μm.

Any natural or synthetic fiber car, be used as the fibrous material. The natural fibers include plant fibers, such as cotton, kapok fiber, wood pulp, non-wood pulp, peanut protein fiber, corn protein fiber, soybean protein fiber, mannan fiber, rubber fiber, hemp, Manila fiber, sisal fiber, New Zealand flax, Luo Buma, coconut, rush, and straw; animal fibers, such as wool, goat hair (including mohair and cashmere), alpaca, angora, camel, vicuna, silk, down, small feather, alginate fiber, chitin fiber, and casein fiber; and mineral fibers, such as asbestos. The synthetic fibers include semi-synthetic ones, such as rayon, viscous rayon, cuprammonium, cellulose acetate, cellulose triacetate fiber, oxidized cellulose acetate, promix, chlorinated rubber, and rubber hydrochloride; and fibers of synthetic polymers, such as nylon, aramid, polyvinyl alcohol, polyvinyl chloride, polyvinylidene chloride, polyester (e.g., polyethylene terephthalate), polyacrylonitrile, acrylic resins, polyethylene, polypropylene, polystyrene, and polyurethane. Metal fiber, carbon fiber, and glass fiber are also usable. Recycled products of these fibrous materials are also useful. Among these fibrous materials particularly preferred are wood pulp, cotton, polyethylene fiber, and polyester fiber in view of their fixing capabilities for the oxidizable metal and the reaction accelerator, flexibility and oxygen permeability of the resulting heat generating sheet 2, and the cost of production.

A combined use of a natural fiber such as wood pulp and a synthetic fiber such as polyethylene fiber or polyester fiber (especially thermoplastic resin fiber) is particularly preferred, because mechanical strength of the resulting molded sheet is prevented from reducing, even if an oxidizable metal is increased. In this case, the mixing ratio of a natural fiber to a synthetic fiber is preferably such that the proportion of a synthetic fiber is 0.1 to 20 parts by weight, more preferably 0.5 to 10 parts by weight, per 100 parts by weight of a natural fiber. The fibrous material, whether natural or synthetic, preferably has an average fiber length of 0.1 to 50 mm, more preferably 0.2 to 20 mm, to secure strength of the heat generating sheet 2 and fiber dispersibility in water.

It is preferred for the fibrous material to have a CSF (Canadian Standard Freeness; JIS P8121) of 600 ml or less, more preferably 450 ml or less. With such a freeness, the fibrous material has satisfactory ability to fix and hold the oxidizable metal, assuring satisfactory heat generation performance of the heat generating sheet 2. Furthermore, it is easy to control the breaking length described later within a specific range described later. As a result, fall-off of the oxidizable metal from the heat generating sheet 2 can be prevented, and the heat generating sheet 2 exhibits adequate mechanical strength. It is desirable for the fibrous material to have as low a CSF as possible. In carrying out papermaking using a slurry containing ordinary pulp fiber as a sole fibrous material and having high contents of other components, the CSF is preferably 100 ml or higher to secure satisfactory drainage and dewatering to provide a molded sheet with a uniform thickness. Moreover, molding defects such as burst of blisters on drying are hardly experienced. Since the proportion of the components other than the fibrous material is relatively high, the slurry shows satisfactory drainage to provide a heat generating sheet 2 with a uniform thickness. A lower CSF indicates a higher fibril content, and a higher fibril content secures better fixation of the components other than the fibrous material on the fibrous material, which results in high sheet strength. The CSF of a fibrous material can be controlled by, for example, the degree of beating. The CSF may also be adjusted by blending fibers different in CSF.

Examples of useful electrolytes include sulfates, carbonates, chlorides, and hydroxides of alkali metals, alkaline earth metals or transition metals. Preferred of them are chlorides of alkali metals, alkaline earth metals or transition metals for their electrical conductivity, chemical stability, and production cost. In particular, sodium chloride, potassium chloride, calcium chloride, magnesium chloride, iron (I) chloride, and iron (II) chloride are more preferred.

If desired, the heat generating sheet 2 can contain additives commonly used in papermaking with no particular restriction. Such additives include flocculants, sizes, colorants, strengthening agents, yield improvers, loading materials, thickeners, pH control agents, and bulking agents.

The heat generating sheet 2 is not limited by the method of making. As described above, since the heat generating sheet is a molded sheet containing an oxidizable metal, a reaction accelerator, and a fibrous material and having incorporated therein an aqueous electrolyte solution, it is obtained by first forming a sheet containing the oxidizable metal, the reaction accelerator, and the fibrous material and then adding an aqueous electrolyte solution to the molded sheet. The sheet formation can be carried out by, for example, wet papermaking taught in JP-A-2003-102761 filed by the same Applicant or extrusion with a die coater. Wet papermaking is preferred for production cost and productivity. Papermaking machines useful for wet papermaking include a cylinder paper machine, a foundrinier paper machine, a short-wire paper machine, and a twin-wire paper machine. The slurry used for wet papermaking contains the oxidizable metal, the reaction accelerator, fibrous material, and water and has a solids content preferably of 0.05% to 10% by weight, more preferably of 0.1% to 2% by weight.

The molded sheet obtained by papermaking is dewatered preferably to a water content of 70% or less (by weight, hereinafter the same), more preferably 60% or less, for assuring shape retention and mechanical strength after papermaking. Dewatering of the molded sheet after papermaking is carried out by, for example, suction, application of pressurized air or pressing with a pressure roll or a pressure plate.

After dewatering, the molded sheet is preferably dried by heating. The heating temperature is preferably 60° to 300° C., more preferably 80° to 250° C. The water content of the molded sheet after drying is preferably 20% or less, more preferably 10% or less. The dewatering step and/or the drying step of the molded sheet are preferably conducted in an inert gas atmosphere to prevent oxidation of the oxidizable metal. Nevertheless, because the molded sheet is free from an electrolyte acting as an oxidation promoter, these steps may be performed in an ordinary air atmosphere if desired, which enables simplification of equipment. The molded sheet after drying contains the oxidizable metal, the reaction accelerator, and the fibrous material. Preferably, the molded sheet after drying contains 60% to 90% by weight, more preferably 70% to 85% by weight, of the oxidizable metal, 5% to 25% by weight, more preferably 8% to 15% by weight, of the reaction accelerator, and 5% to 35% by weight, more preferably 10% to 20% by weight, of the fibrous material.

The thickness of the resulting molded sheet (i.e., the heat generating sheet 2 before addition of water) is preferably 0.1 to 2 mm, more preferably 0.15 to 1.5 mm to have both mechanical strength and flexibility for a good fit to a part of the body. For the same reason, the grammage of the molded sheet is preferably 10 to 1000 g/m$^2$, more preferably 50 to 600 g/m$^2$, even more preferably 100 to 500 g/m$^2$.

A plurality of the molded sheets can be used as stacked on each other. The molded sheet can be used as folded, and a plurality of the folded sheets may be stacked on each other. The weight ratio of the molded sheet to the area of the steam generating warming sheet 1 is preferably 0.03/cm$^2$ to 0.17 g/cm$^2$, more preferably 0.06 g/cm$^2$ to 0.14 g/cm$^2$, to attain a desired temperature duration and a good fit without inviting manufacturing disadvantages. For the same reason, the weight to unit area ratio of the oxidizable metal is preferably 0.02 g/cm to 0.14 g/cm$^2$, more preferably 0.04 g/cm$^2$ to 0.12 g/cm$^2$.

To prevent fall-off of the oxidizable metal from the molded sheet during use of the steam generating warming sheet 1 and to assure the flexibility of the molded sheet, the molded sheet preferably has a breaking length of 200 to 4000 m, more preferably 200 to 3000 m, as measured in accordance with JIS P8113 (hereinafter the same). A molded sheet having a breaking length falling within the recited range is obtained easily by using a fibrous material having the above-specified CSF.

The molded sheet thus prepared is then impregnated with an aqueous electrolyte solution to obtain the heat generating sheet 2. This step is desirably conducted in an inert gas atmosphere of nitrogen, argon, etc. Impregnation with an aqueous electrolyte solution can be carried out by spraying, brush coating, dip coating, gravure coating, reverse coating, doctor blade coating or the like method. The electrolyte concentration of the aqueous solution and the amount of the solution to be added are adjusted so that the contents of the electrolyte and water in the resulting heat generating sheet 2 may fall within the respective ranges recited previously.

The resulting heat generating sheet 2 is put in the holder 3 to make the steam-generating warming sheet 1. The steam-generating warming sheet 1 is preferably air-tightly packaged in a wrapper made of an oxygen barrier material to be supplied as an individually packaged steam-generating warming sheet. On use, the steam generating warming sheet 1 is taken out of the package, whereupon the oxidizable metal contained in the steam-generating warming sheet 1 reacts with oxygen in air to start heat generation and, at the same time, generates steam. Materials of such oxygen barrier wrapper preferably include those having an oxygen transmission rate (ASTM D3985) of 10 $cm^3 \cdot mm/(m^2 \cdot d \cdot MPa)$ or lower, more preferably 2 $cm^3 \cdot mm/(m^2 \cdot d \cdot MPa)$ or lower, such as an ethylene-vinyl alcohol copolymer and polyacrylonitrile.

In another embodiment, the molded sheet contains the oxidizable metal, the reaction accelerator, the fibrous material, and the electrolyte. The molded sheet of this embodiment becomes a heat generating sheet on addition of water. In this case, the molded sheet contains 50% to 85% by weight, preferably 65% to 80% by weight, of the oxidizable metal, 4.5% to 25% by weight, preferably 7.0% to 15% by weight, of the reaction accelerator, 4.5% to 35% by weight, preferably 9% to 20% by weight, of the fibrous material, and 0.004% to 11% by weight, preferably 0.005% to 7% by weight, of the electrolyte. To make the heat generating sheet, 30% to 80% by weight, preferably 40% to 70% by weight, of water is added per 100 parts by weight of the molded sheet.

In still another embodiment, the molded sheet contains the oxidizable metal, the reaction accelerator, the fibrous material, and water. The molded sheet of this embodiment becomes a heat generating sheet on addition of an electrolyte. In this case, the molded sheet contains 30% to 65% by weight, preferably 40% to 55% by weight, of the oxidizable metal, 2.5% to 20% by weight, preferably 4.0% to 10% by weight, of the reaction accelerator, 2.5% to 30% by weight, preferably 5.0% to 15% by weight, of the fibrous material, and 25% to 45% by weight, preferably 30% to 40% by weight, of water. To make the heat generating sheet, 0.2% to 10% by weight, preferably 0.5% to 5% by weight, of the electrolyte is added per 100 parts by weight of the molded sheet.

The package containing the steam-generating warming sheet 1 is preferably labeled to indicate that the steam-generating warming sheet 1 is for improving human body's physiology. For example, the package may be labeled to the effect that application to the lower back reduces or eliminates lower back pain or that application to the abdomen reduces or eliminates abdominal pain or that application to the lower back and/or the abdomen improves the gastrointestinal functions and helps recover from fatigue. Consumers will be informed by this labeling that the steam-generating warming sheet of the present invention achieves physiology improving effects that have heretofore been impossible with conventionally known disposable body warmers. Thus, the good value of the improved performance of the present invention will easily be recognized by consumers. The labeling can contain any kind of information means for conveying information about the improved performance to consumers, including signs and graphics as well as characters. The labeling may contain information to the effect that the product of the present invention is superior to other commercial products. In addition to, or in place of, the labeling on the package, instructions containing the contents of the labeling may be put in the package together with the steam generating warming sheet 1. The labeling may be printed directly on the steam-generating warming sheet 1.

Figure 5A:
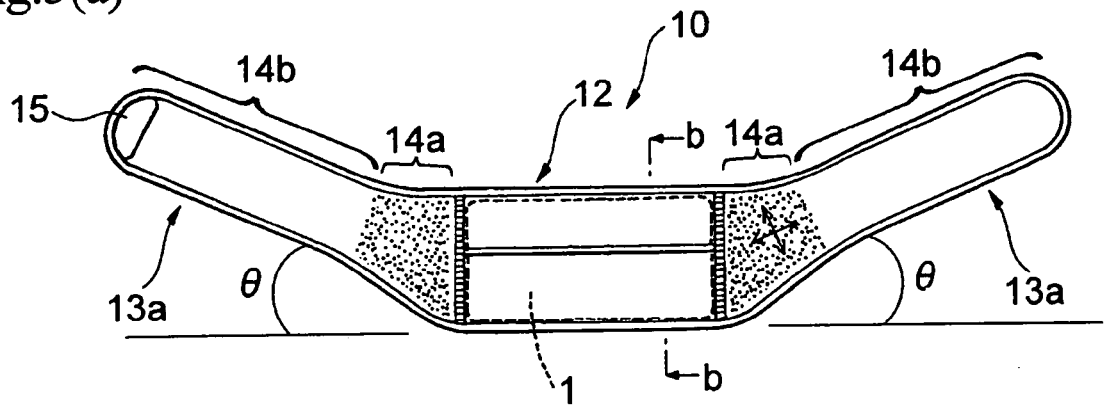
FIG. 5(a) is a plan view of an attachment belt for supporting the steam-generating warming sheet of FIG. 1.
Figure 5B:
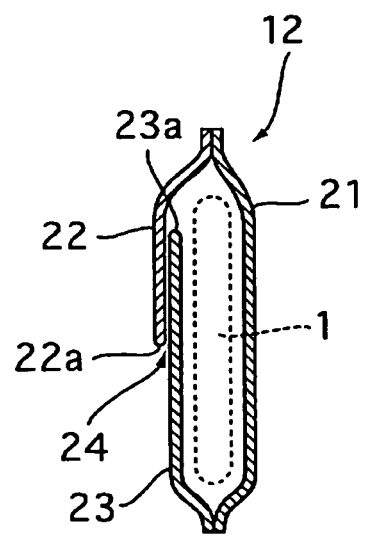
FIG. 5(b) is a cross-section taking along line b-b in FIG. 5(a).

The steam generating warming sheets 1 shown in FIGS. 1 and 2 can be applied to the body by putting into an attachment belt shown in FIGS. 5(a) and 5(b) and attaching the belt around the body. The attachment belt 10 shown in FIGS. 5(a) and 5(b) has a rectangular holding part 12 which can hold and support the steam-generating warming sheet 1 and a pair of arms, a first arm 13a and a second arm 13b, extending from the opposing sides of the holding part 12. The first arm 13a and the second arm 13b are symmetrical. The first and the second arms 13a and 13b make an angle θ with a horizontal line H extending in the longitudinal direction of the attachment belt 10.

A fastening means 15, such as a hook member of a hook-and-loop mechanical fastener, is attached to the body-facing side (the paper face of FIG. 5(a)) of the end of the first arm 13a, while a landing member (not shown) on which the fastening means 15 is fixed, such as a loop member of a hook-and-loop mechanical fastener, is attached to the outer side (the side opposite to the paper face of FIG. 5(a)) of the second arm 13b.

The first and the second arms 13a and 13b are each composed of a basal part 14a nearer to the holding part 12 and a free end part 14b nearer to the arm end. The basal part 14a has its width decreasing toward the free end part 14b. The basal part 14a and the free end part 14b connect to each other at the position where the width of the basal part 14a no longer decreases. The basal part 14a preferably has stretchability in both the extending direction of the arms 13a and 13b and the direction perpendicular to that direction (indicated by the two-headed arrows in FIG. 5(a)). For that purpose, the basal part 14a is preferably made of two-way stretchable fabric.

The outer panel 21 is preferably made of fabric with an agreeable feel. It is preferred for the outer panel 21 to have sufficient air permeability. The outer panel 21 is made of, for example, tricot fabric. Similarly, the first skin facing panel 22 and the second skin facing panel 23 are preferably made of fabric with an agreeable feel. It is preferred for the first and the second skin facing panels 22 and 23 to be made of materials having sufficient water vapor permeability. Such materials include knitted mesh fabric.

The holding part 12 is composed of three panels 21, 22, and 23, sewn together 20 to make a bag. The outer panel 21 is provided on the outer face of the attachment belt 10 and has a rectangular shape. The first skin facing panel 22 and the second skin facing panel 23 are provided on the skin facing side of the attachment belt 10 and have a rectangular shape. All the first and the second skin facing panels 22 and 23 and the outer panel 21 have the same length in the horizontal direction. The width of the two skin facing panels 22 and 23 is smaller than that of the outer panel 21 in the vertical direction. The first skin facing panel 22 is sewn together with the outer panel 21 along its upper side and both lateral sides. The second skin facing panel 23 is sewn together with the outer panel 21 along its lower side and both lateral sides. The lower part of the first skin facing panel 22 and the upper part of the second skin facing panel 23 overlap with each other, with the lower edge 22a of the first skin facing panel 22 and the upper edge 23a of the second skin facing panel 23 being free edges. Thus, the holding part 12 has formed on its skin facing side an opening 24 extending transversely across the holding part 12. The steam-generating warming sheet 1 is put inside the holding part 12 through the opening 24. As stated, the lower part of the first skin facing panel 22 and the upper part of the second skin facing panel 23 overlap with each other so that the steam generating warming sheet 1 once put into the holding part 12 hardly comes out of the holding part 12 and is stably held in the holding part 12. Since the size of the opening 24 is large enough and it is easy to open, the steam generating warming sheet 1 is easy to put in and take out.

Figure 6A:
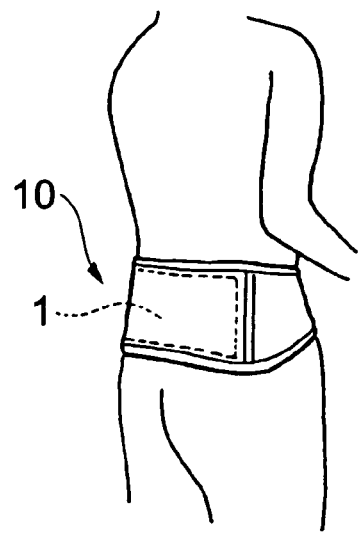
FIG. 6(a) illustrates a way of applying the steam-generating warming sheet of FIG. 1 to the lower back.
Figure 6B:
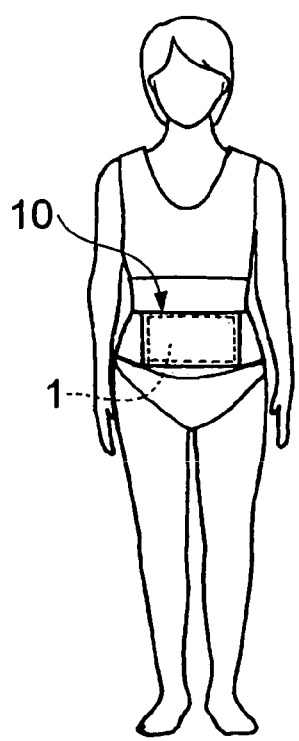
FIG. 6(b) illustrates a way of applying the steam-generating warming sheet of FIG. 1 to the abdomen.

The steam-generating warming sheet 1 held in the attachment belt 10 is applied, e.g., to the lower back or the abdomen of the body as illustrated in FIGS. 6(a) and 6(b). The attachment belt 10 is worn by attaching the attachment belt 10 around the waist and engaging the fastening means (not shown) attached to the first arm 13a with the landing member (not shown) attached to the second arm 13b. In this case, the steam-generating warming sheet 1 faces the body surface via the water vapor-permeable first and second skin facing panels 22 and 23.

Figure 7:
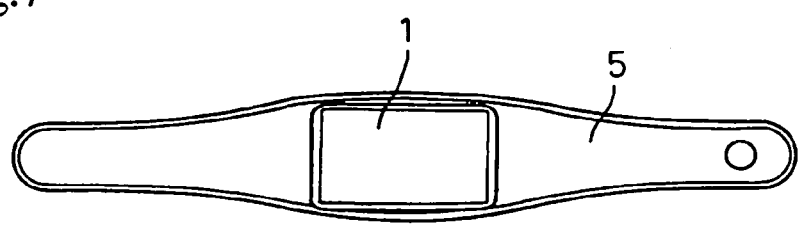
FIG. 7 illustrates an example of the mode of use of the steam-generating warming sheet shown in FIG. 3.

When the steam-generating warming sheet takes on the structure shown in FIGS. 3 and 4, it is used as fixed to an attachment belt 5 shown in FIG. 7. The attachment belt 5 has a constant width in its central part and a slightly decreasing width toward both ends. A fastener, such as a mechanical fastener member, is attached to one end of the belt. The fastener is adapted to be engaged with the other end of the belt. The attachment belt 5 is made of a stretchable material to provide a good fit to the wearer's body.

On use, release paper (not shown) covering the moisture hardly-permeable film of the holder 3 is stripped off to expose the adhesive layer 4 (see FIG. 4). The steam generating warming sheet is attached to the inner side of the central part of the attachment belt 5 on its adhesive layer 4. Thus, the moisture permeable film side, namely the air permeable side faces outside. The attachment belt 5 is then applied to the lower back of a wearer with the steam-generating warming sheet 1 directly facing to the wearer's body, and both ends of the belt 5 are overlapped on the side of the wearer's abdomen to have the fastener on one end engaged with the other end. The attachment belt 5 is thus fixed. Since the wearer-facing side of the steam-generating warming sheet 1 is the nonwoven fabric 3C having an agreeable hand (see FIG. 4), the steam generating warming sheet 1 gives no discomfort to the wearer while being worn. In this way, the steam-generating warming sheet 1 supplies warming steam to the wearer for a prescribed time period (e.g., about 3 to 5 hours) to exert a desired effect and efficacy.

The present invention is not limited to the foregoing embodiments. For example, While the steam-generating warming sheet 1 according to the foregoing embodiments is preferably applied as a steam-generating warming article to the lower back or the shoulder(s) to elevate the deep body temperatures, it is also applicable to other parts of the body, such as the neck, shoulders, back, abdomen, elbows, and knees. The steam generating warming sheet 1 may be used for skin care applications, such as facial and body cleansing or sanitization and makeup removal. The steam-generating warming sheet 1 may also be applied to objects other than human bodies in combination with various functional agents for cleaning/sanitization, slow release of wax, perfuming, deodorization, and the like in home care applications such as cleaning of wood or tatami floors, stoves, and ventilating fans or car care applications such as washing and waxing.

EXAMPLES

Example 1

A steam-generating warming article (steam generating warming sheet) of the embodiment illustrated in FIGS. 1 and 2 was prepared.

(1) Formulation of Raw Material Composition

Fibrous material: pulp fiber NBKP (Mackenzie (trade name) from Fletcher Challenge Canada, Ltd.; CSF: 140 ml) 8 wt %

Oxidizable metal: iron powder (RKH (trade name) from Dowa Iron Powder Co., Ltd.) 84 wt %

Reaction accelerator: activated carbon (Carboraffin (trade name) from Japan EnviroChemicals, Ltd.) 8 wt %

To the composition of the above components were added 0.7 parts by weight of a polyamide-epichlorohydrin resin (WS4020 (trade name) from Seiko PMC Corp.) as a cationic flocculant and 0.18 parts by weight of sodium carboxymethyl cellulose (HE1500F (trade name) from Dai-ichi Kogyo Seiyaku Co., Ltd.) as an anionic flocculant per 100 parts by weight of the solids content of the raw material composition (i.e., the total of the fibrous material, the oxidizable metal, and the moisture retaining agent). Water (industrial water) was added thereto to result in a solids concentration of 12% by weight.

(2) Papermaking Conditions

The raw material composition was diluted with water to a concentration of 0.3% by weight immediately before the head box. The resulting slurry was formed into a sheet on an inclined short-wire paper machine at a line speed of 15 m/min to prepare a wet molded sheet.

(3) Drying Conditions

The wet molded sheet was dewatered between felt blankets, passed as such between 140° C. heated rolls to be dried to a water content of 5 wt % or less to obtain a molded sheet (heat generating sheet precursor) having a grammage of 450 g/m$^2$ and a thickness of 0.45 mm. As a result of measurement with a thermogravimetric analyzer (TG/DTA 6200 from Seiko Instruments Inc.), the resulting heat generating sheet precursor was found to be made up of 84 wt % iron, 8 wt % activated carbon, and 8 wt % pulp.

(4) Preparation of Heat Generating Sheet

The molded sheet (heat generating sheet precursor) was cut to 80 mm width and 100 mm length. Two cut pieces were stacked, and 50 parts by weight of an electrolytic solution described below was syringed into the stack per 100 parts by weight of the stack and penetrated throughout the two thicknesses of the sheet by capillarity to obtain a stack of heat generating sheets (heat generating molded sheets).

Electrolytic solution:

Electrolyte: purified salt (NaCl)

Water: industrial water

Concentration: 5 wt %

(5) Putting in Holder

A bag (holder) shown in FIGS. 1 and 2 was made using a moisture permeable film of calcium carbonate-containing polyethylene (WVTR: 800 to 1200 g/m$^2$·24 hr; air permeance: 10000±2000 s/100 cm$^3$), a moisture impermeable sheet of linear low density polyethylene, and air-through nonwoven fabric. The two thicknesses of the heat generating sheet were put into the bag to obtain a steam-generating warming sheet shown in FIGS. 1 and 2. The steam release area was 0.016 m².

(6) Evaluation-1

To demonstrate physiology improving effects of the resulting steam-generating warming sheet, a clinical test on lower back pain reducing effects was carried out.

The steam-generating warming sheet was put into the holding part 12 of the attachment belt 10 shown in FIGS. 5(a) and 5(b) and applied to the lower back of each test subject. The test subjects were divided into a group in which the steam generating warming sheet was applied with its steam release side facing the wearer's lower back (moist heat group) and a group in which the opposite side faced the wearer's lower back (dry heat group). Moist heat is applied to the lower back in the moist heat group. In the dry heat group, no steam but dry heat was applied. The moist heat group consisted of 28 test subjects, and the dry heat group 27. The test subjects were males and females aged 23 to 67 years who had been aware of lower back pain or lower back and leg pain for the last at least 6 months. The symptoms of the subjects of the two groups before the testing were as shown in Table 1 below. The subjects wore the steam-generating warming sheet 8 hours a day for 4 consecutive weeks and rated their back pain after detaching the steam-generating warming sheet everyday in accordance with the following score: 1=no pain; 2=occasional light pain; 3=constant pain sometimes with considerable pain; 4=constant severe pain.

Figure 8A:
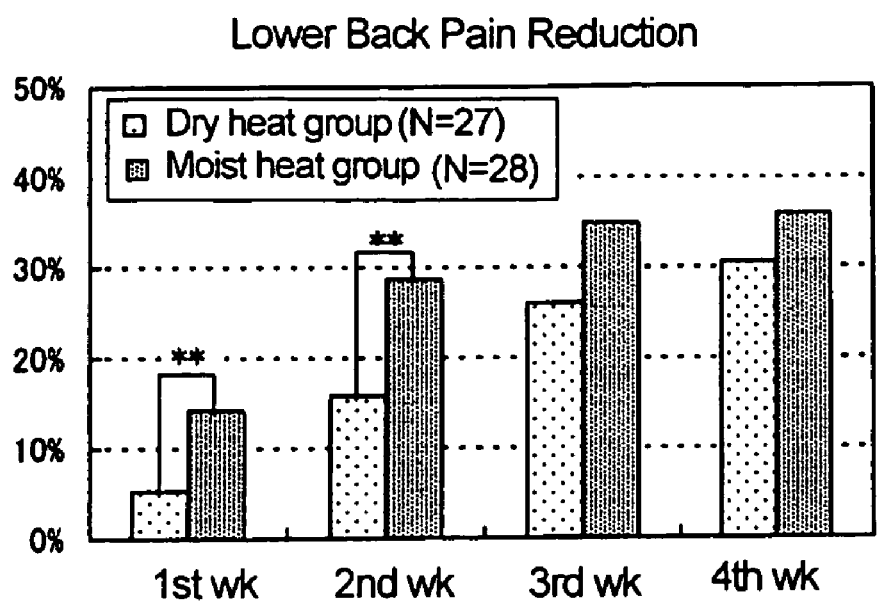
FIG. 8(a) is a graph showing the lower back pain reducing effect by a steam-generating warming article according to the present invention.
Figure 8B:
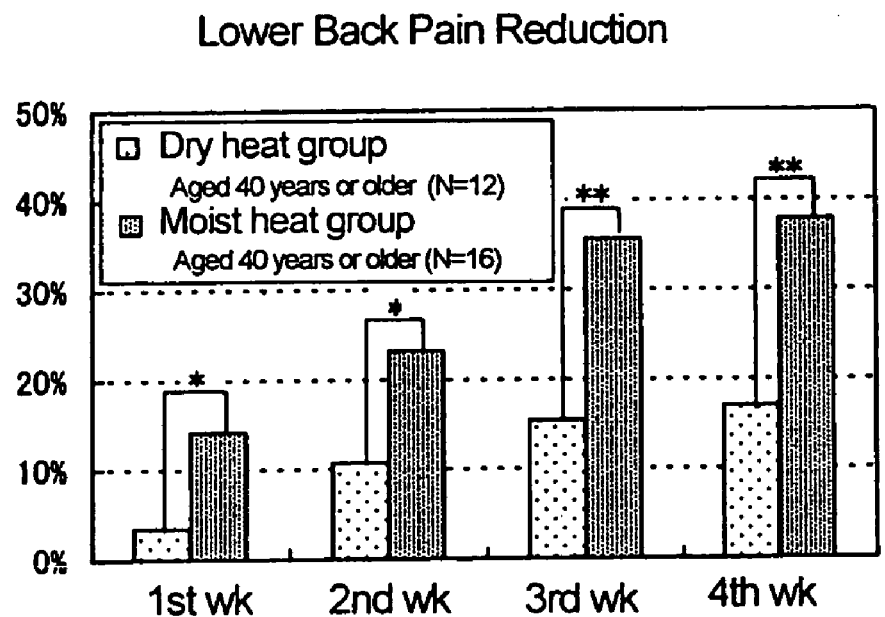
FIG. 8(b) is a graph showing the lower back pain reducing effect by a steam-generating warming article according to the present invention.
Figure 9A:
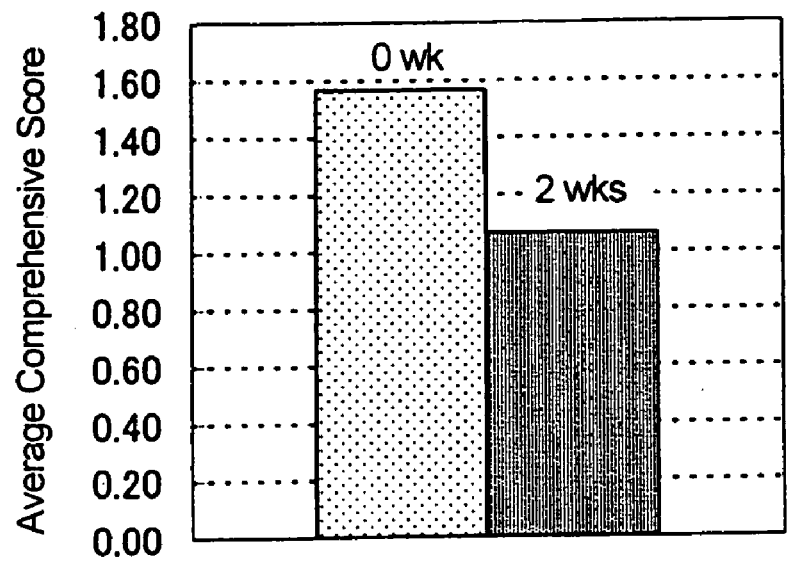
FIG. 9(a) is a graph showing the lower back pain reducing effect by a steam-generating warming article according to the present invention.
Figure 9B:
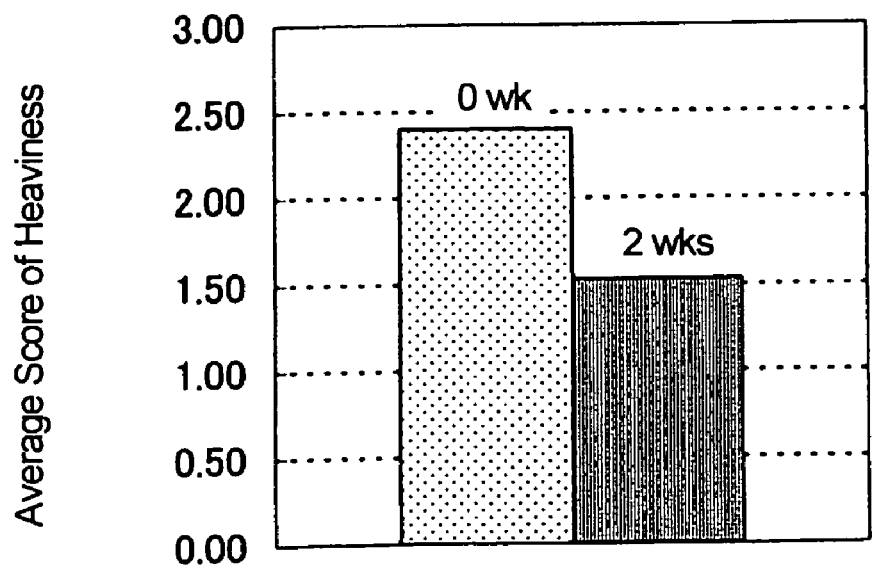
FIG. 9(b) is a graph showing the lower back pain reducing effect by a steam-generating warming article according to the present invention.
Figure 9C:
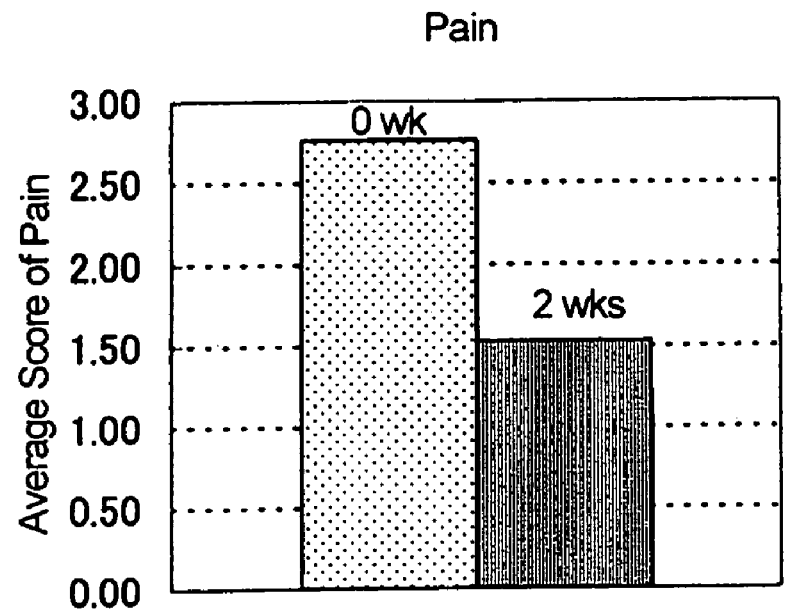
FIG. 9(c) is a graph showing the lower back pain reducing effect by a steam-generating warming article according to the present invention.
Figure 9D:
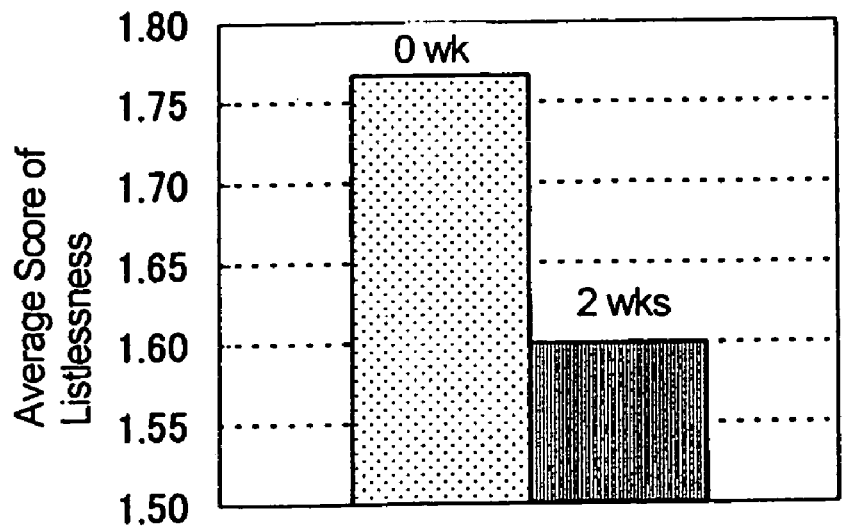
FIG. 9(d) is a graph showing the lower back pain reducing effect by a steam-generating warming article according to the present invention.
Figure 10A:
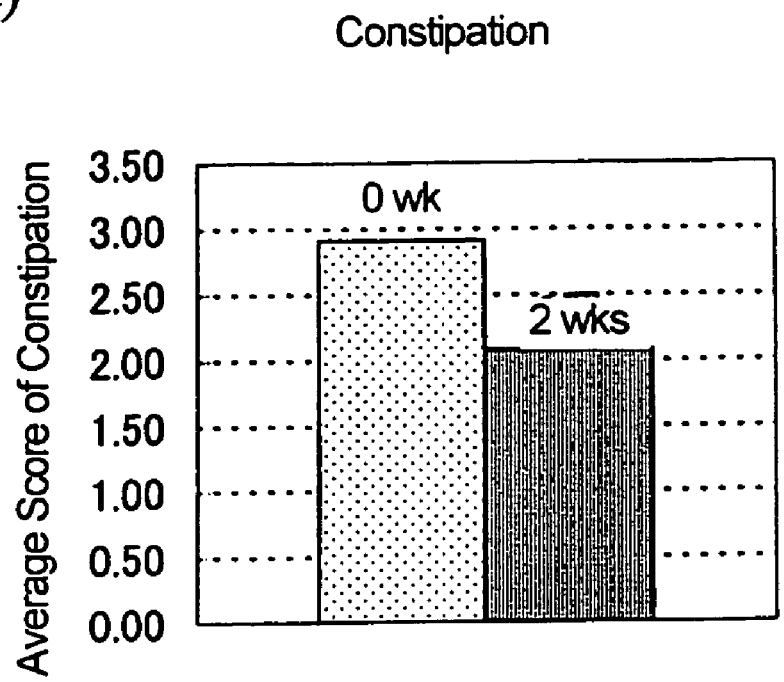
FIG. 10(a) a graph showing the abdominal symptom reducing effect by a steam-generating warming article according to the present invention.
Figure 10B:
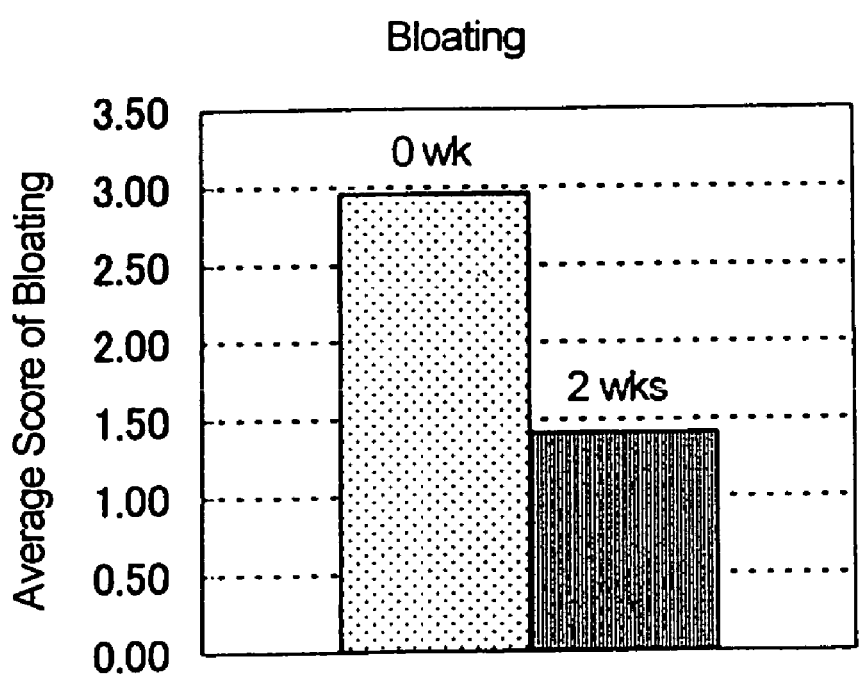
FIG. 10(b) a graph showing the abdominal symptom reducing effect by a steam-generating warming article according to the present invention.
Figure 10C:
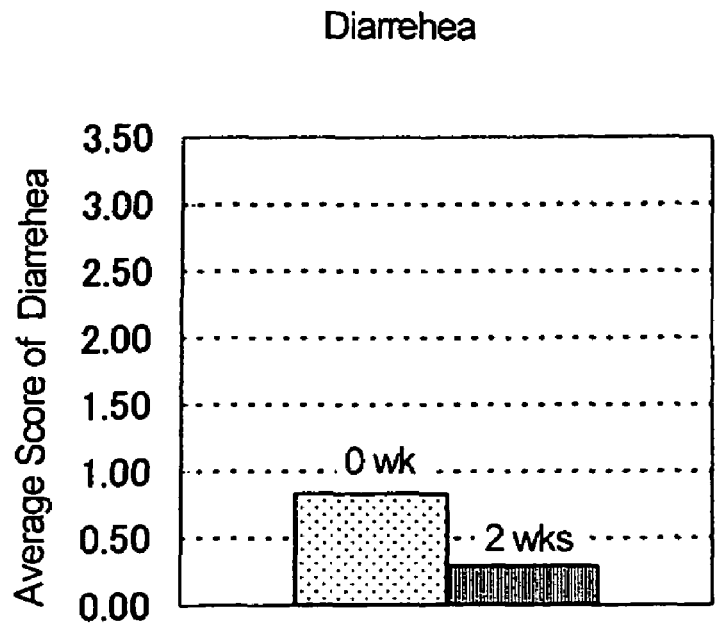
FIG. 10(c) a graph showing the abdominal symptom reducing effect by a steam-generating warming article according to the present invention.
Figure 10D:
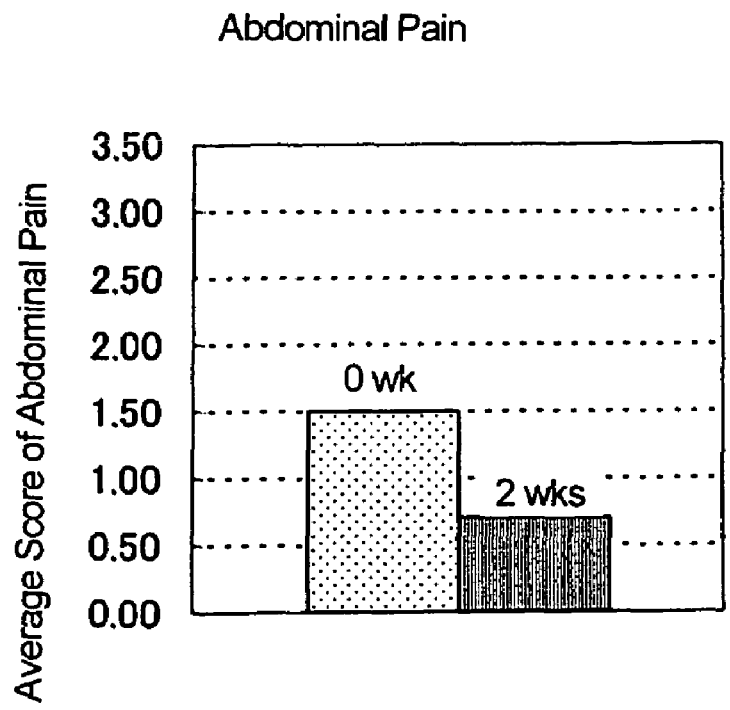
FIG. 10(d) a graph showing the abdominal symptom reducing effect by a steam-generating warming article according to the present invention.

The scores were added up and averaged every week for each group. The percentage of the subjects who rated 1 was taken as a cure rate, provided that those who rated the pain as 1 immediately before the start of the testing were counted out. The change in cure rate was compared between the moist heat group and the dry heat group every week. The results are graphically shown in FIGS. 8(a) and 8(b). FIG. 8(a) shows the results of all the test subjects, and FIG. 8(b) the results of those aged 40 years or more. In FIGS. 8(a) and 8(b), the mark * indicates that probability P in the $x^2$ test is less than 0.03, and the mark ** indicates that the probability P in the same test is less than 0.01. Both indicate that the difference is statistically significant.

Separately, moist heat characteristics of the steam-generating warming sheet were measured while worn by the subjects of the moist heat group. The results obtained are shown in Table 2.

As is apparent from the results in FIGS. 8(a) and 8(b), the lower back pain is reduced more in the moist heat group than in the dry heat group. In particular, it is seen that the lower back pain reducing effect is significantly pronounced on the subjects aged 40 years or older, the middle and older generations suffering from lower back pain.

TABLE 1

|  | Moist Heat Group | Dry Heat Group |
| --- | --- | --- |
| No lower back pain | 0% | 0% |
| Occasional light pain | 50% | 50% |
| Constant pain | 42% | 40% |
| Constant severe pain | 8% | 10% |

TABLE 2

| Duration of Skin Surface Temp. of 38-49° C. | Cumulative Amount of Steam Released | Highest Temp. Reached |
| --- | --- | --- |
| 6.5 hrs | 6.3 mg/3 hrs · cm² | 48° C. |

(7) Evaluation-2

A clinical test different from the evaluation-1 was conducted to examine lower back pain reducing effects. The test group was only a moist heat group consisting of 30 females aged 45 to 64 years who suffered from chronic lower back pain. The test subjects wore the steam generating warming sheet 8 hours a day for 2 consecutive weeks and rated their lower back pain with respect to each of the three symptoms, (1) pain, (2) heaviness, and (3) listlessness, after detaching the steam-generating warming sheet everyday in accordance with the following scores: 0=no symptom; 1=not so uneasy; 2=slightly uneasy; 3=uneasy; 4=very uneasy.

After wearing for 2 weeks, the scores of all the subjects were added up and averaged for each symptom, and the average score was compared with that before the testing. Furthermore, all the scores were added up and averaged to make a comprehensive evaluation. The results are graphically represented in FIGS. 9(a) through 9(d).

As is apparent from the results shown in FIGS. 9(a) to 9(d), applying the steam-generating warming sheet to the lower back for two weeks proved obviously effective in reducing lower back pain.

(8) Evaluation-3

Improving effects on abdominal symptoms were clinically tested. The test group was a moist heat group consisting of 25 females aged 45 to 64 years who had abdominal symptoms. The test subjects wore the steam generating warming sheet in a fashion illustrated in FIG. 6(b) 8 hours a day for 2 consecutive weeks and rated their abdominal conditions everyday after detaching the steam-generating warming sheet in terms of the following symptoms: (1) constipation, (2) diarrhea, (3) bloating, and (4) pain in accordance with the following scores: 0=no symptom; 1=not so uneasy; 2=slightly uneasy; 3=uneasy; 4=very uneasy.

After the two week test, the scores of all the subjects were added up and averaged for each symptom, and the average score was compared with that before the testing. The results are graphically shown in FIGS. 10(a) through 10(d).

As is apparent from the results in FIGS. 10(a) to 10(d), applying the steam-generating warming sheet to the abdomen for 2 weeks proves obviously effective in improving the abdominal symptoms.

Example 2

(1) Formulation of Slurry

Oxidizable Metal:

iron powder RKH (trade name) produced by Dowa Iron Powder Co., Ltd. 160 g

Fibrous Material:

Pulp fiber (NBKP) Skeena (trade name) produced by Skeena; average fiber length: 2.1 mm 20 g Reaction Accelerator:

Activated carbon Carboraffin (trade name) available from Takeda Chemical Industries, Ltd. 20 g Flocculant:

Sodium carboxymethyl cellulose Cellogen WS-C (trade name) produced by Dai-ichi Kogyo Seiyaku Co., Ltd. 0.5 g Polyamide-epichlorohydrin resin WS547 (trade name) produced by Japan PMC Corp. 0.5 g Water: Industrial water 99800 g (2) Papermaking Conditions A wet molded sheet was prepared from the slurry by papermaking using a small-sized, inclined short-wire paper machine (possessed by Kochi Prefectural Paper Technology Center) at a line speed of 7 m/min.

(3) Dewatering and Drying Conditions

The wet sheet was pressed between two felt pieces for dewatering and passed as pressed through a pair of rolls heated to 120° C. at a line speed of 7 m/min for drying to a water content of 5% by weight or lower. The resulting molded sheet had a grammage of 180 g/m². The thickness of the molded sheet is shown in Table 3.

(4) Condition of Addition of Aqueous Electrolyte Solution

Four molded sheets thus obtained were stacked on each other, and an aqueous solution of electrolyte described below was sprayed thereon to obtain a set of heat generating sheets having a water content of 39%. The composition of the heat generating sheet is shown in Table 3.

Electrolytic Solution:
Electrolyte: purified salt (NaCl)
Water: industrial water
Concentration: 5 wt %

(5) Putting in Holder

A bag (holder) shown in FIGS. 3 and 4 was made using a moisture permeable film of calcium carbonate-containing polyethylene (WVTR: 800 g/m²·24 hr; air permeance: 10000 sec/100 cm³), a moisture impermeable sheet of linear low density polyethylene, and air-through nonwoven fabric. The set of the heat generating sheets was put into the bag to obtain a steam-generating warming sheet shown in FIGS. 3 and 4.

Examples 3 to 8 and Comparative Examples 1 to 4

Steam-generating warming sheets were prepared in the same manner as in Example 2, except for changing the composition of the heat generating sheets as shown in FIG. 5. In Comparative Example 4, the steam generating warming sheet was prepared using the following slurry formulation.

Oxidizable Metal:
iron powder RKH (trade name) produced by Dowa Iron Powder Co., Ltd. 96 g Fibrous Material:
Pulp fiber (NBKP) Skeena (trade name) produced by Skeena; average fiber length: 2.1 mm 12 g Reaction Accelerator:
Activated carbon Carboraffin (trade name) available from Takeda Chemical Industries, Ltd. 12 g Flocculant:
Sodium carboxymethyl cellulose Cellogen WS-C (trade name) produced by Dai-ichi Kogyo Seiyaku Co., Ltd. 0.5 g
Polyamide-epichlorohydrin resin WS547 (trade name) produced by Japan PMC Corp. 0.3 g
Water: Industrial water 99800 g Examples 9 to 12

Steam-generating warming sheets were prepared in the same manner as in Example 2, except that holes or cuts were made in the molded sheet as shown in Table 5.

Evaluation:

The steam-generating warming sheets obtained in Examples 2 to 8 and Comparative Examples 1 to 4 were evaluated by measuring the highest temperature reached by the warming steam, the duration of 40° C. warming steam release, and the cumulative amount of warming steam released in 90 minutes from the contact with air. The highest temperature reached was measured in accordance with JIS S4100. The term "highest temperature reached" denotes a highest temperature reached as measured by the JIS method. If the highest temperature reached is as low as less than 38° C., the deep body temperature does not rise, resulting in no warming up of the whole body. If the highest temperature reached is 60° C. or higher, the sheet is too hot to use. The steam generating warming sheet was attached to the attachment belt shown in FIG. 7 and applied to the lower back of a test subject, and the deep body temperature was measured in accordance with the method below. Furthermore, the ratio of the subjects who felt warmed up was obtained as follows. The results of the evaluation are shown in Table 4.

The steam-generating warming sheets obtained in Examples 9 to 12 were evaluated by measuring the highest temperature reached and the duration of 40° C. warming steam release. They were applied to the part of a test subject's body indicated in Table 5 and evaluated for fit to that part and capability of giving the wearer a physical feeling of being warmed up. The results obtained are shown in Table 5.

(a) Deep Body Temperature Measurement

A deep body thermometer Coretemp CM-210 equipped with a deep body temperature probe PD1, both from Terumo Corp., was attached to the wearer's body just above the part where the steam-generating warming sheet was applied in an environment of 20° C. and 40% RH. Before applying the steam-generating warming sheet, the deep body thermometer was attached to the body. After the reading became stable, the steam generating warming sheet was applied for 60 minutes, and the deep body temperature was read. The deep body temperature as measured with a deep body temperature probe PD1 is believed to correspond to the tissue temperature 10 mm deep from the skin. The deep body temperature before applying the steam-generating warming sheet was taken as A, while the highest deep body temperature during the measurement as B. The difference of B minus A was identified as the rise in deep body temperature.

(b) Ratio of Subjects who felt Warmed Up

Ten test subjects wore the steam-generating warming sheet for 60 minutes in an environment of 20° C. and 40% RH and were asked whether or not they felt warmed up. The percentage of the subjects who answered yes was obtained.

TABLE 3

| | | Heat Generating Sheet | | | | | | Molded Sheet | Molded Sheet Weight Ratio per |
| --- | --- | --- | --- | --- | --- | --- | --- | --- | --- |
| | | Composition (wt %) | | | | Weight Ratio | | | Steam-generating |
| | | Pulp | Activated Carbon | Iron Powder | Electrolyte | Water | Pulp/Iron powder | Activated Carbon/Iron Powder | Thickness (mm) | Warming Sheet Unit Area (g/cm²) |
| Examples | 2 | 6 | 6 | 47 | 2 | 39 | 0.13 | 0.13 | 0.28 | 0.064 |
| | 3 | 6 | 9 | 44 | 2 | 39 | 0.13 | 0.2 | 0.3 | 0.063 |

TABLE 3-continued

| | | Heat Generating Sheet | | | | | | Molded Sheet Thickness (mm) | Molded Sheet Weight Ratio per Steam-generating Warming Sheet Unit Area (g/cm²) |
|---|---|---|---|---|---|---|---|---|---|
| | | Composition (wt %) | | | | Weight Ratio | | | |
| | | Pulp | Activated Carbon | Iron Powder | Electrolyte | Water | Pulp/Iron powder | Activated Carbon/Iron Powder | | |
| | 4 | 8.5 | 8.5 | 42 | 2 | 39 | 0.19 | 0.19 | 0.3 | 0.063 |
| | 5 | 9 | 6 | 44 | 2 | 39 | 0.2 | 0.13 | 0.31 | 0.066 |
| | 6 | 9 | 9 | 41 | 2 | 39 | 0.21 | 0.21 | 0.32 | 0.065 |
| | 7 | 12 | 5 | 42 | 2 | 39 | 0.28 | 0.11 | 0.33 | 0.068 |
| | 8 | 11 | 6 | 42 | 2 | 39 | 0.25 | 0.14 | 0.33 | 0.064 |
| Comparative Examples | 1 | 18 | 9 | 32 | 2 | 39 | 0.56 | 0.28 | 0.35 | 0.07 |
| | 2 | 12 | 2 | 45 | 2 | 39 | 0.27 | 0.04 | 0.3 | 0.067 |
| | 3 | 9 | 5 | 37 | 3 | 46 | 0.24 | 0.14 | 0.33 | 0.067 |
| | 4 | 6 | 6 | 47 | 2 | 39 | 0.13 | 0.13 | 0.16 | 0.029 |

TABLE 4

| | Highest Temp. Reached (° C.) | Duration of Warming Steam | Cumulative Amount of Released Warming Steam (mg/cm²) | Deep Body Temp. (° C.) | Ratio of Subjects who Felt Warmed up (%) |
|---|---|---|---|---|---|
| Example 2 | 43.1 | 5 hrs 20 mins | 5.25 | 0.4 | 100 |
| Example 3 | 45.1 | 4 hrs 40 mins | 5.25 | 0.4 | 100 |
| Example 4 | 49.6 | 4 hrs 10 mins | 4.55 | 0.4 | 100 |
| Example 5 | 43.3 | 4 hrs 40 mins | 3.15 | 0.3 | 100 |
| Example 6 | 47.1 | 4 hrs | 4.73 | 0.4 | 100 |
| Example 7 | 43.7 | 4 hrs 30 mins | 2.63 | 0.3 | 100 |
| Example 8 | 43.9 | 4 hrs 10 mins | 3.5 | 0.3 | 100 |
| Comparative Example 1 | 44.8 | 2 hrs 10 mins | 2.19 | 0.2 | 50 |
| Comparative Example 2 | 42.3 | 3 hrs** | 2.13 | 0.1 | 20 |
| Comparative Example 3 | 41.5 | 2 hrs 40 mins | 1.74 | 0.1 | 10 |
| Comparative Example 4 | 40.5 | 2 hrs | 2.18 | 0.1 | 20 |
| Referential Example 1* | 50.3 | 10 hrs | 1.46 | 0.1 | 0 |

*Commercially available disposable heat pack body warmer
**Rise of temperature is slow

TABLE 5

| | Geometry of Holes or Cuts | Highest Temp. Reached (° C.) | Duration | Application Part of Body | Fit | Feeling of being Warmed up |
|---|---|---|---|---|---|---|
| Example 9 | 2 holes/cm², 5 mm² each | 45 | 5 hrs 50 mins | lower back | Good | constantly yes |
| Example 10 | cuts at 5 mm interval | 43.5 | 5 hrs 30 mins | lower back | Good | constantly yes |
| Example 11 | 2 holes, each of 5 mm², per cm² and cuts at 5 mm interval | 45.2 | 5 hrs 50 mins | lower back | Good | constantly yes |
| Example 12 | 2 holes, each of 5 mm², per cm² and cuts at 5 mm interval | 45.2 | 5 hrs 50 mins | Elbow | good | constantly yes |

As is apparent from the results in Table 4, the steam-generating warming sheet of Examples reach 40° C. or higher and continued releasing warming steam of 40° C. for as long as more than 3 hours. In Comparative Examples 1 to 4, on the other hand, the duration is short, the cumulative amount of released warming steam is small, and no increase in deep body temperature is achieved. In Reference Example 1 testing a commercially available disposable heat pack body warmer that does not release moist heat, although the reachable temperature is high, the amount of steam is small, and no increase in deep body temperature is obtained. It is obviously understandable from this comparison that the steam generating warming sheets of Examples are effective in elevating the deep body temperature.

As demonstrated in Table 5, the steam-generating warming sheets having holes or cuts exhibit improved temperature characteristics (the highest temperature and the duration) to give a wearer a soothing feeling (fit and feeling of being warmed up).

INDUSTRIAL APPLICABILITY

The present invention brings about improvements on physiology of the human body, such as the reduction or elimination of pains including lower back pain and abdominal pain, improvement on functions of visceral organs such as gastrointestinal, and recovery from physical fatigue.

The invention claimed is:

1. A steam-generating warming article comprising a steam generating warming sheet which is adapted to supply steam while in contact with the surface of the body,
    wherein said steam generating warming sheet comprises a heat generating sheet having a large number of holes or cuts and a holder for holding said heat generating sheet, said heat generating sheet being a molded sheet comprising an oxidizable metal, a reaction accelerator, and a fibrous material, having incorporated therein an aqueous electrolyte solution, and wherein said heat generating sheet generates heat upon contact with air,
    wherein the molded sheet contains 60% to 90% by weight of the oxidizable metal, 5% to 25% by weight of the reaction accelerator, and 5% to 35% by weight of the fibrous material, and
    wherein the heat generating sheet comprises
    40 to 80 parts by weight of the aqueous electrolyte solution containing 1% to 15% by weight of an electrolyte per 100 parts by weight of the molded sheet
    said holder having air permeability in at least a part thereof to allow steam to be released outside through said holder, and
    an air permeable part of said holder having a water vapor transmission rate of 300 to 2000 g/m$^2$·24 hr (JIS Z0208, 40° C. 90% RH).

2. The steam-generating warming article according to claim 1, wherein the steam-generating warming sheet has a steam release area of 0.001 to 0.25 m$^2$.

3. The steam-generating warming sheet article according to claim 1, wherein a weight ratio of the reaction accelerator to the oxidizable metal is 0.1 to 0.3, and a weight ratio of the fibrous material to the oxidizable metal is 0.1 to 0.3.

4. The steam-generating warming article according to claim 1, wherein a ratio of the weight of the molded sheet to the area of the steam-generating warming sheet is 0.03 g/cm$^2$ to 0.17 g/cm$^2$.

5. The steam-generating warming article according to claim 1, wherein the molded sheet has a thickness of 0.1 mm to 2 mm.

6. The steam-generating warming article according to claim 1, wherein the molded sheet is a sheet formed by a papermaking process.

7. The steam-generating warming article according to claim 1, which is used as supported in or on an attachment belt with the air permeable part of the holder facing outward.

8. A package of a steam-generating warming article comprising an oxygen barrier wrapper and the steam-generating warming article according to claim 1, air-tightly packaged in the wrapper.

9. A method of improving a human body's physiology comprising contacting a human body surface with the steam-generating warming article of claim 1.

10. The method according to claim 9, wherein said steam-generating warming article is applied to the lower back to reduce or eliminate lower back pain.

11. The method according to claim 9, wherein said steam-generating warming article is applied to the abdomen to reduce or eliminate abdominal pain.

12. The method according to claim 9, wherein said steam-generating warming article is applied to the lower back and/or the abdomen to improve the gastrointestinal functions.

13. The method according to claim 9, wherein said steam-generating warming article is applied to the lower back and/or the abdomen to help recover from fatigue.

14. The method according to claim 9, wherein said steam-generating warming article is applied to the human body surface to supply steam and maintain the skin surface temperature at 38° to 49° C. over a period of 3 to 15 hours.

* * * * *

UNITED STATES PATENT AND TRADEMARK OFFICE
CERTIFICATE OF CORRECTION

PATENT NO. : 7,652,228 B2 Page 1 of 1
APPLICATION NO. : 10/582232
DATED : January 26, 2010
INVENTOR(S) : Igaki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 631 days.

Signed and Sealed this

Twenty-third Day of November, 2010

David J. Kappos
*Director of the United States Patent and Trademark Office*